US007824717B2

(12) United States Patent
Stäb et al.

(10) Patent No.: US 7,824,717 B2
(45) Date of Patent: Nov. 2, 2010

(54) USE OF LICOCHALCONE A AGAINST ROSACEA

(75) Inventors: Franz Stäb, Echem (DE); Rainer Wolber, Hamburg (DE); Christopher Mummert, Bienenbüttel (DE); Ludger Kolbe, Dohren (DE); Jan Batzer, Hamburg (DE); Kerstin Eggers, Wulfsen (DE); Anette Bürger, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 11/586,538

(22) Filed: Oct. 26, 2006

(65) Prior Publication Data

US 2007/0134194 A1 Jun. 14, 2007

Related U.S. Application Data

(62) Division of application No. 10/985,733, filed on Nov. 10, 2004.

(30) Foreign Application Priority Data

Nov. 10, 2003 (DE) ................. 103 52 367

(51) Int. Cl.
*A61K 36/48* (2006.01)
(52) U.S. Cl. .................................... 424/757
(58) Field of Classification Search ........... None
See application file for complete search history.

(56) References Cited

U.S. PATENT DOCUMENTS

| 6,174,534 | B1 * | 1/2001 | Richard et al. .............. 424/401 |
| 6,485,756 | B1 | 11/2002 | Aust et al. |
| 6,492,326 | B1 | 12/2002 | Robinson et al. |
| 2002/0115622 | A1 | 8/2002 | Kumagai et al. |
| 2005/0037042 | A1 | 2/2005 | Dieck et al. |
| 2005/0048007 | A1 | 3/2005 | Ruggles |
| 2005/0136139 | A1 | 6/2005 | Kruse et al. |
| 2005/0158259 | A1 | 7/2005 | Kropke et al. |
| 2005/0158350 | A1 | 7/2005 | Max et al. |
| 2005/0191266 | A1 | 9/2005 | Raschke et al. |
| 2005/0201967 | A1 | 9/2005 | Albrecht et al. |

FOREIGN PATENT DOCUMENTS

| DE | 20318416 | | 4/2004 |
| JP | 04297418 | A * | 10/1992 |
| JP | 09227353 | | 9/1997 |
| JP | 10-077221 | | 3/1998 |
| JP | 2001-163718 | | 6/2001 |
| JP | 2001163718 | A * | 6/2001 |
| JP | 2003-238379 | | 8/2003 |
| WO | 00/13685 | | 3/2000 |
| WO | 03/015808 | | 2/2003 |

OTHER PUBLICATIONS

Djaković et al. "Rosacea as a multisystemic disease." Srp Arh Celok Lek., vol. 131, No. 11-12 (Nov.-Dec. 2003) 474-8, PubMed abstract only.*
Shibata et al. "Inhibitory effects of licochalcone A isolated from *Glycyrrhiza inflatai* root on inflammatory ear edema and tumour promotion in mice". Planta Med. No. 57, vol. 3 (Jun. 1991) 221-224, PubMed Abstract.*
International Rosacea Foundation. Retrieved the Internet on: Sep. 1, 2008. Retrieved from: <http://www.internationalrosaceafoundation.org/>.*
U.S. Appl. No. 10/571,530, filed Mar. 10, 2006 and entitled "Use of licochalcone A or of an extract containing licochalcone A from radix glycyrrhizae inflatae against aging skin".
U.S. Appl. No. 10/581,271, filed Jun. 1, 2006 and entitled "Combination of 2,3-dibenzylbutyrolactone and licochalcone-A".
U.S. Appl. No. 11/514,214, filed Sep. 1, 2006 and entitled "Active substance combination of licochalcone A and phenoxyethanol".
U.S. Appl. No. 11/586,538, filed Oct. 26, 2006 and entitled "Use of licochalcone A against rosacea".
English Language Abstract of JP 2003-238379.
Barfod L., et al., "Chalcones from Chinese Liquorice Inhibit Proliferation of T Cells and Production of Cytokines", Int. Immunopharmacol., 2002, vol. 2(4), pp. 545-555.
Graf, J., "Herbal Anti-Inflammatory Agents for Skin Disease", Skin Therapy Letter, 2000, vol. 5(4), pp. 3-5.
Kobayashi S., et al., "Inhibitory Effect of Isoliquiritin, a Compound in Licorice Root, on Angiogenesis in Vivo and Tube Formation in Vitro", Bio. Pharm. Bull., 1995, vol. 18(10), pp. 1382-1386.
Tsutsumi T., et al., "Introduction to New Functions of Natural Plant Extracts and Their Application to Cosmetics", Fragrance Journal, 2001, vol. 29(1), pp. 93-96.
European Search Report dated Apr. 12, 2005 for European Application No. 04 10 5498.
German Search Report dated Jun. 15, 2004 for German Application No. DE 103 56 869.7.
Tsukiyama R-I, Katsura H, Tokuriki N, Kobayashi M. Antimicrob Agents Chemother. 2002; 46(5): 1226-1230.
http://web.archive.org/web/*/http://www.kaviskin.com/skin_care.php (web Publication date: Jul. 27, 2003). Date Accessed: Jan. 18, 2007.
http://web.archive.org/web/*/http://www.eltean.com.skin.htm (Web Publication Date: Apr. 6, 2001). Date Accessed: Jan. 19, 2007.
http://web.archive.org/*/http://www.herbasin.com/database/gancao.htm (Accessed Dec. 8, 2005).
Sovak M, AL Seligson, M Konas, M Hajduch, M. Dolezal, M Machala, R. Nagourney, J. Natl Cancer inst. 2002; 94(17): 1275-1281 (Especially p. 1280).
http://www.ibiblio.org/pfaf/cgi-bin/arr_html?Glycyrrhiza+glabra (Accessed Dec. 13, 2005).
http://web.archive.org/web/*/http://bodd.cf.ac.uk/botDermFolder/BotDermL/LEGU.html glabra (Accessed Dec. 13, 2005).

* cited by examiner

*Primary Examiner*—Amy L Clark
(74) *Attorney, Agent, or Firm*—Greenblum & Bernstein, P.L.C.

(57) ABSTRACT

The present invention relates to the use of licochalcone A for the treatment of rosacea.

20 Claims, No Drawings

USE OF LICOCHALCONE A AGAINST ROSACEA

CROSS-REFERENCE TO RELATED APPLICATIONS

The present application is a divisional of U.S. application Ser. No. 10/985,733, filed Nov. 10, 2004, the entire disclosure whereof is expressly incorporated by reference herein, which claims priority under 35 U.S.C. §119 of German Patent Application No. 103 52 367.7, filed Nov. 10, 2003.

FIELD OF THE INVENTION

The invention relates to the use of licochalcone A and licochalcone A-containing extracts for the treatment of rosacea.

BACKGROUND

The skin is the largest organ of humans. It has to fulfill a plurality of vital functions, for example, the regulation of heat, and the barrier function against drying of the skin and the entire organism. It also has to act as a protective mechanism against penetration and absorption of extrinsic substances. This barrier function is realized by the epidermis which forms as outermost layer the actual protective cover against the environment. With about one tenth of the total thickness, it is at the same time the thinnest layer of the skin.

The skin is subjected to a plurality of physical, chemical, and biological stresses. A plurality of these stresses lead—for different reasons—to a temporary or permanent redness of the skin. These stresses include, for example, inflammations of the skin, skin reactions, dermographism, soreness of the skin (for example, from dermatitis or contact dermatitis, such as diaper rash), creeping eruption, erysipelas, herpes zoster, frostbite, diphtheria, liver cirrhosis, gout, burns, or allergic reactions.

A special form of skin redness is rosacea. Roseceal [lat. rosaceus >rose-colored<], also known as facial telangiectasis, copper nose, or brandy face, is a chronic disease of the facial skin that occurs in most cases only in middle and older ages and affects in particular the region of the nose, and also the forehead and cheeks (butterfly rash). The dilation of the surface vessels of the skin leads in part to deep red accumulations of blood, dilated vessels (telangiectasias), depending on the form, also to scaling of the skin, gradual formation of papules or pustules, and later (in most cases only in men) to the formation of a rhinophyma. Suspected causes include instability of the vasomotor nerves with a seborrhoeic constitution, endocrine disorders, chronic gastrointestinal diseases, and focal infections; there possibly exists a genetic disposition. Alcohol abuse can likewise be of importance. Treatment occurs locally with antibiotics (Source: Brockhaus—Die Enzyklopaedie: 24 volumes. 20th revised edition. Leipzig, Mannheim: F. A. Brockhaus 1996-99).

Skin rednesses in general and rosacea in particular present great physical and psychological stress to the affected person. Likewise, a viewer sees them in most cases as optically little attractive, sickly, and in-aesthetic.

It is therefore an object of the present invention to develop agents and preparations which clearly improve the optical appearance of the skin parts that are affected by rosacea. It is intended to develop agents and preparations which allow the rosacea of the skin to disappear, to suppress it over a longer period, and to prevent its reappearance to a great extent. In this connection, it is desired that the agents and preparations be especially tolerable to the skin and exhibit little toxicity. In their application, they are expected to show no side effects as are known from pharmaceuticals.

Surprisingly, the objects are accomplished by:
a) the use of licochalcone A for the treatment of rosacea;
b) the use of cosmetic or dermatological preparations containing licochalcone A for the treatment of rosacea;
c) the use of aqueous extracts from the radix glycyrrhizae inflatae for the treatment of rosacea; and
d) the use of cosmetic or dermatological preparations containing aqueous extracts from the radix glycyrrhizae inflatae for the treatment of rosacea.

SUMMARY OF THE INVENTION

The present invention provides a method of treating rosacea. The method comprises the application of Licochalcone A to an area in need of treatment of rosacea.

In one aspect of the method, the Licochalcone A may be applied in the form of a cosmetic or dermatological preparation which comprises Licochalcone A. For example, the preparation may comprise Licochalcone A in a concentration of from 0.0001 wt. % to 5 wt. %, e.g., from 0.001 wt. % to 1 wt. %, based on the total weight of the preparation.

In another aspect of the method, the Licochalcone A may be applied in the form of a cosmetic or dermatological preparation which comprises an aqueous extract of Radix Glycyrrhiza inflata. For example, the aqueous extract may be present in a concentration of from 0.001 wt. % to 10 wt. %, from 0.01 wt. % to 2 wt. %, e.g., based on the total weight of the preparation.

In yet another aspect, the preparation may further comprise one or more polyols such as, e.g., butylene glycol and glycerol. For example, the one or more polyols may be present in a concentration of from 0.001 wt. % to 10 wt. %, e.g., from 0.05 wt. % to 5 wt. %, based on the total weight of the preparation.

In a still further aspect, the preparation may further comprise water.

The present invention also provides a method of treating rosacea, which method comprises applying an aqueous extract of Radix Glycyrrhiza inflata to an area in need of treatment of rosacea.

In one aspect of the method, the aqueous extract may be applied in the form of a cosmetic or dermatological preparation. For example, the aqueous extract may be present in a concentration of from 0.001 wt. % to 10 wt. %, e.g. from 0.01 wt. % to 2 wt. %, based on the total weight of the preparation.

In yet another aspect, the preparation may further comprise one or more polyols such as, e.g., butylene glycol and glycerol. For example, the one or more polyols may be present in a concentration of from 0.001 wt. % to 10 wt. %, e.g., from 0.05 wt. % to 5 wt. %, based on the total weight of the preparation.

DETAILED DESCRIPTION OF THE INVENTION

The skin parts that were treated with the active constituents or preparations of the invention showed a clearly healthier appearance over a longer period. It was clearly possible to reduce the appearance of the rosacea and to treat the rosacea.

The plant species glycyrrhiza inflata belongs in the same way as the officinal licorice glycyrrhiza glabra in Europe to the species of the glycyrrhiza that is a member of the fabaceae (pea plant) family. The drug radix glycyrrhiza inflatae, i.e., the root of the plant is commonly used, for example, in the medicine of the Far East.

A constituent of the aqueous extract from the radix glycyrrhizae inflatae is licochalcone A which is characterized by the following structural formula:

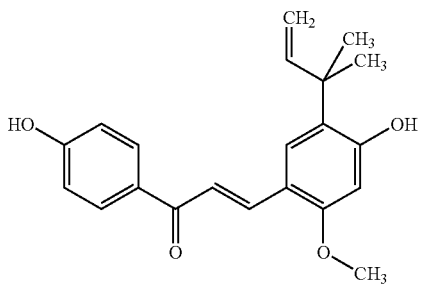

It is assumed that this substance has its share in the effect as is provided by the invention, possibly in synergy with the other constituents of the extract.

In accordance with the invention, it will be especially advantageous, when the preparations contain licochalcone A in amounts from 0.0001 to 5 wt. %, in particular 0.001 to 1 wt. %, very particularly 0.005 to 0.15 wt. %, each based on the total weight of the preparation.

In accordance with the invention, it will also be very advantageous, when the preparations contain 0.001 to 10 wt. %, in particular 0.05 to 5 wt. %, very particularly 0.01 to 2 wt. % of one or more polyols based on the total weight of the preparation.

In accordance with the invention, it will also be advantageous, when the preparations contain licochalcone A as a constituent of vegetable extracts, in particular of the radix glycyrrhizae inflatae.

In accordance with the invention, it will also be advantageous, when licochalcone A is present in the form of an aqueous extract that contains:

licochalcone A,
water, and
if need be, one or more polyols.

In accordance with the invention, it will be advantageous, when the cosmetic or dermatological preparations contain an aqueous extract from the radix glycyrrhizae inflatae in a range from 0.001 to 10 wt. %, in particular 0.05 to 5 wt. %, very particularly 0.01 to 2 wt. % based on the total weight of the preparation.

In accordance with the invention, it will be advantageous, when the cosmetic or dermatological preparations contain one or more polyols in a range from 0.001-10 wt. %, in particular 0.05-5 wt. %, very particularly 0.01-2 wt. % based on the total weight of the preparation. In particular, it will be advantageous to select butylene glycol as the polyol.

It is very advantageous to proceed from an extractt that is marketed by Maruzen under the name Polyol Soluble Licorice Extract P-U.

Furthermore, it is advantageous to use licochalcone A in other vehicle systems in a concentration from 0.0001 to 5 wt. %, in particular 0.001 to 1 wt. %, very particularly 0.0005 to 0.05 wt. %.

With that, the invention also provides a method for combating rosacea characterized in that the active constituent combinations that are used in accordance with the invention are brought into contact with the area that is affected by the rosacea by means of a suitable cosmetic or dermatological vehicle.

In accordance with the invention, it may be advantageous to add to the preparations of the invention additional active agents for the treatment of skin redness and/or rosacea, for example, selected from the group of anti-inflammatory substances, such as, for example, allantoin, tannin, antihistamines, antiphlogistics, glucocorticoids (e.g., hydrocortisone), polydocanol, as well as plant substances, such as azulen, bisabolol, glycyrrhizin, hamamelin, and plant extracts, such as chamomile. In accordance with the invention, the bisabolol compounds are preferred.

One or more of these anti-inflammatory substances can be advantageously contained in the preparation in a total concentration of 0.01-5 wt. %, preferably in a concentration of 0.1-1 wt. %, and very preferably in a concentration of 0.2-0.75 wt. %, each based on the total weight of the concentration.

Likewise, the combination of licochalcone A or aqueous extracts from the radix glycyrrhizae inflatae with niacinamide and/or panthenol will be advantageous in accordance with the invention, when it contains these compounds in a concentration from 0.01 to 5 wt. % based on the total weight of the preparation.

The combination of individual or several substances selected from the foregoing group with the use of the active constituents according to the invention leads to a synergistic increase of the effect of the individual substances and, thus, amounts to an independent invention.

The constituents used in accordance with the invention can be easily incorporated into common cosmetic or dermatological formulations, advantageously into pump sprays, aerosol sprays, creams, ointments, tinctures, lotions, or the like.

It is also possible and, if need be, advantageous to combine the active constituents as are used in accordance with the invention with other constituents, for example, with other antimicrobial, antimycotic, or antiviral substances.

It is advantageous to buffer the compositions of the invention. Of advantage is a pH range from 3.5 to 7.5. It is especially advantageous to choose the pH value in a range from 4.0 to 6.5.

The cosmetic or dermatological formulations of the invention can have the customary composition, and be, used for the treatment of the skin and/or hair for the purposes of a dermatological treatment, or a treatment for the purposes of cosmetic care. However, they can also be used for makeup products in decorative cosmetics.

For their use, the cosmetic and dermatological formulations of the invention are applied, as is usual for cosmetics and dermatics, in an adequate quantity to the skin and/or hair.

In accordance with the invention, it is possible to use customary antioxidants in preparations which contain the active constituent combinations of the invention. Advantageously, such antioxidants are selected from the group comprising amino acids (for example, glycine, histidine, tyrosine, tryptophane) and their derivatives, imidazoles (for example, urocanic acid) and their derivatives, peptides, such as D,L-camosine, Dcamosine, L-camosine, and their derivatives (for example; anserine), carotenoids, carotenes (for example, α-carotene, β-carotene, lycopene) and their derivatives, lipoic acid and its derivatives (for example, dihydrolipoic acid), aurothioglucose, propylthiouracil, and other thiols (for example, thioredoxin, glutathione, cysteine, cystine, cystamine, and their glycosyl-, N-acetyl-, methyl-, ethyl-, propyl-, amyl-, butyl- and lauryl-, palmitoyl-, oleyl-, γ-linoleyl-, cholesteryl-, and glyceryl esters), as well as their salts, dilauryl thiodipropionate, distearyl thiodipropionate, thiodipropionic acid and its derivatives (esters, ethers, peptides, lipids, nucleotides, nucleosides, and salts), as well as sulfoximine compounds (for example, buthionine sulfoximine, homocysteine sulfoximine, buthionine sulfones, penta-, hexa-, heptathionine sulfoximine), in very low, tolerable dosages (for example, pmol to µmol/kg), furthermore (metallic) chelating agents (for example, α-hydroxy fatty acids, palmitic acid, phytic acid, lactoferrin), α-hydroxy acids (for example, citric acid, lactic acid, malic acid), humic acid, bile acid, bile extracts, bilirubin, biliverdin, EDTA, EGTA, and their derivatives, unsaturated fatty acids and their derivatives (for example, γ-linolenic acid, linoleic acid, oleic acid), folic acid, and their derivatives, alanine diacetic acid, flavonoids, polyphenoles, catechins, vitamin C and derivatives (for example, ascorbyl palmitate, Mg-ascorbyl phosphate, ascorbyl acetate); tocopherols and derivatives (for example, vitamin E acetate), as well as coniferyl benzoate of the benzoin resin, rutic acid and its derivatives, butyl hydroxytoluene, butyl hydroxyanisole, nordihydroguaiac resin acid, nordihydroguaiaretic acid, trihydroxy butyrophenone, uric acid and its derivatives; mannose and its derivatives, zinc and its derivatives (for example, ZnO, $ZnSO_4$), selenium and its derivatives (for example, selenium methionine), stilbene and its derivatives (for example, stilbene oxide, trans-stilbene oxide), and the derivatives (salts, esters, ethers, sugars, nucleotides, nucleosides, peptides, and lipids) of these aforesaid active constituents, which are suitable in accordance with the invention.

The quantity of the foregoing antioxidants (one or more compounds) in the preparations is preferably 0.001-30 wt. %, very preferably 0.05-20 wt. %, in particular 110 wt. % based on the total weight of the preparation.

The prophylaxis or the cosmetic or dermatological treatment with the active constituent as is used in accordance with the invention, or with the cosmetic or topical dermatological preparations with an effective content of the active constituent as is used in accordance with the invention occurs in the usual manner such that the active constituent of the invention or the cosmetic or topical dermatological preparations having an effective content of the active constituent of the invention is applied to the affected places of the skin.

It is possible and advantageous to incorporate the active constituent as is used in accordance with the invention into customary cosmetic or dermatological preparations which can be present in various forms. For example, they may be a solution, an emulsion of the water-in-oil (W/O) type or oil-in-water (O/W) type, or a multiphase emulsion, for example, of the water-in-oil-in-water (W/O/W) type or of the oil-in-water-in-oil (O/W/O) type, a hydrodispersion or lipodispersion, a gel, a solid stick, an ointment, or also an aerosol.

For the purposes of the present invention, emulsions of the invention, for example, in the form of a cream, a lotion, a cosmetic milk, are advantageous and contain, for example, fats, oils, waxes, and/or other lipoids, as well as water and one or more elmusifiers as are customarily used for such a type of formulation.

For the purposes of the present invention, it is also possible and advantageous to include the active constituent as used in accordance with the invention in aqueous systems or surfactant preparations for cleansing the skin and hair.

Naturally, a skilled person is aware that demanding cosmetic compositions are in most cases not possible without the customary auxiliaries and additives. These include, for example, consistency substances, fillers, perfume, dyes, emulsifiers, additional active constituents, such as vitamins or proteins, light protectants, stabilizers, insect repellants, alcohol, water, salts, antimicrobial, proteolytic, or keratolytic agents, etc.

Corresponding requirements apply, mutatis mutandis, to the formulation of medical preparations.

For the purposes of the present invention, medical compositions for topical application normally contain one or more medicaments in an effective concentration. For the sake of simplicity, the legal provisions of the Federal Republic of Germany (for example, Cosmetics Regulations, Food and Drug Law) are herewith incorporated by reference for a clear distinction between cosmetic and medical applications.

In this connection, it is also of advantage to add the active constituent as used in accordance with the invention as an additive to preparations that already contain other active constituents for other purposes.

For example, for the purposes of the present invention, it is advantageous to use a content of UV protective substances.

Advantageously, preparations of the present invention may therefore contain substances, which absorb W radiation in the UVB range, where the total amount of the filter substances is, for example, from 0.1 wt. % to 30 wt. %, preferably 0.5 wt. % to 10 wt. %, in particular 1.0 to 6.0 wt. % based on the total weight of the preparations.

The UVB filters may be oil-soluble or water-soluble. In accordance with the invention, oil-soluble UVB filters include, for example:
  derivatives of 3-benzylidene camphor, preferably 3-(4-methylbenzylidene) camphor;
  derivatives of 4-aminobenzoic acid, preferably 2-(ethylhexyl)4-dimethylamino-benzoate, amyl 4-(dimethylamino)-benzoate;
  esters of cinnamic acid, preferably (2-ethylhexyl)4-methoxy cinnamate, isopentyl 4-methoxy cinnamate;
  esters of salicylic acid, preferably (2-ethylhexyl) salicylicate, (4-isopropylbenzyl) salicylicate, homomenthyl salicylicate;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzalmalonic acid, preferably di(2-ethylhexyl) 4-methoxybenzalmalonate; and
  2,4,6-trianilino-(p-carbo-2'-ethyl-1'-hexyloxy)-1,3,5-triazine.

Advantageous water-soluble UVB filters are, for example:
  2-phenylbenzimidazole-5-sulfonic acid and its salts, such as its sodium-, potassium-, or its triethanol ammonium salts;
  sulfonic acid derivatives of benzophenones, preferably, 2-hydroxy-4-methoxybenzophenone-5-sulfonic acid and its salts; and
  sulfonic acid derivatives of 3-benzylidene camphor, such as, for example, 4-(2-oxo-3-bornylidene-methyl)benzenesulfonic acid, 2-methyl-5-(2-oxo-3bornylidenemethyl)sulfonic acid and their salts.

Naturally, the list of the referenced UVB filters, which may be used in accordance with the invention, is not intended to be limiting.

It may also be of advantage to use in the preparations of the invention UVA filters, which are normally present in cosmetic and/or dermatological preparations. These filter substances are preferably derivatives of dibenzoylmethane, in particular 1-(4'-tertbutylphenyl)-3-(4'-methoxyphenyl)propane-1,3-dione and 1-phenyl-3-(4'isopropylphenyl)propane-1,3-dione. Likewise these preparations, which contain these combinations, are subject matter of the invention. The amounts used for UVA filter substances can be the same as the amounts for the UVB filter substances.

For the purposes of the present invention, cosmetic and/or dermatological preparations may also contain inorganic pigments, which are normally used in cosmetics for protecting the skin against UV radiation. These pigments are oxides of the titanium, zinc, zirconium, silicon, manganese, cerium, and mixtures thereof, as well as modifications, wherein the oxides are the active agents. Very preferred are the pigments on the basis of titanium oxide. The amounts used can be the same as the amounts for the foregoing combinations.

Advantageously, the cosmetic and dermatological preparations can contain constituents and auxiliaries as are normally used for this type of preparations, for example, antioxidants, preservatives, bactericides, perfumes, antifoaming substances, dyes, pigments that have a coloring effect, thickeners, surfactants, emulsifiers, softening, moisturizers and/or humectants, fats, oils, waxes, or other common constituents of a cosmetic or dermatological formulation, such as alcohols, polyols, polymers, foam stabilizers, electrolytes, organic solvents, or silicone derivatives.

Provided that the cosmetic or dermatological preparation for the purposes of the present invention constitutes a solution, or emulsion, or dispersion, it is possible to use as solvents:
  water or aqueous solutions;
  oils, such as triglycerides of the capric or caprylic acid, preferably, however, castor oil;
  fats, waxes, and other natural and synthetic lipids, preferably esters of fatty acids with alcohols having a low number of C atoms, for example, isopropanol, propylene glycol or glycerin, or esters of fatty alcohols with alkanoic acids having a low number of C atoms, or with fatty acids;
  alcohols, diols, or polyols having a low number of C atoms, as well as their ethers, preferably ethanol, isopropanol, polypropylene glycol, glycerin, ethyleneglycol, ethyleneglycol monoethyl- or -monobutyl ether, polypropylene glycolmonomethyl, -monoethyl-, or -monobutyl ether, diethyleneglycol monomethyl- or mono ethyl- ether, and analogous products.

In particular, mixtures of the aforesaid solvents are used. In the case of all alcoholic solvents, water may be a further constituent.

The oil phase of the emulsions, oleogels, or hydrodispersions or lipodispersions for the purposes of the present invention is advantageously selected from the group of the esters of saturated and/or unsaturated, branched and/or unbranched alkanecarboxylic acids with a chain length of 3 to 30 C atoms, and saturated and/or unsaturated, branched or unbranched alcohols with a chain length from 3 to 30 C atoms from the group of the esters from aromatic carboxylic acids, and saturated and/or unsaturated, branched and/or unbranched alcohols with a chain length from 3 to 30 C atoms. Such ester oils can then be advantageously selected from the group of isopropylmyristate, isopropylpalmitate, isopropylstearate, isopropyloleate, n-butylstearate, n-hexyllaureate, n-decyloleate, isooctylstearate, isononylstearate, isononylisononanoate, 2-ethylhexylpalmitate, 2-ethylhexyllaureate, 2-hexyldecylstearate, 2-octyldocecylpalmiate, oleyloleate, oleylerucate, erucylerucate, as well as synthetic, semisynthetic, and natural mixtures of such esters, for example, jojoba oil.

Furthermore, one may advantageously select the oil phase from the group of branched and unbranched hydrocarbons and hydrocarbon waxes, silicone oils, dialkylether, of the group of saturated or unsaturated, branched or unbranched alcohols, as well as the fatty acid triglycerides, namely the triglycerin ester of saturated and/or unsaturated, branched and/or unbranched alkanoic acids of a chain length from 8 to 24, in particular 12 to 18 C atoms. One may advantageously select the fatty acid triglycerides, for example, from the group of the synthetic, semisynthetic, and natural oils, for example, olive oil, sunflower oil, soy bean oil, peanut oil, rape seed oil, almond oil, palm oil, coconut oil, palm kernel oil, and more of the like.

Likewise any desired mixtures of such oil and wax components are to be advantageously used for the purposes of the present invention. If need be, it can also be advantageous to use waxes, for example, cetylpalmitate as the sole lipid component of the oil phase.

The oil phase is advantageously chosen from the group of 2-ethylhexylisostearate, octyldodecanol, isotridecyl isononanoate, isoeicosane, 2-ethylhexylcocoate, $C_{12-15}$-alkylbenzoate, caprylic/capric acid triglyceride, and dicaprylether.

Especially advantageous are mixtures of $C_{12-15}$-alkylbenzoate and 2-ethyihexylisostearate, mixtures of $C_{12-15}$-alkylbenozate and isotridecyl isononanoate, as well as mixtures of $C_{12-15}$-alkylbenzoate, 2-ethylhexylisostearate and isotridecylisononanoate.

Of the hydrocarbons, one can advantageously use for the purposes of the present invention, paraffinic acid, squalane and squalene.

Advantageously, the oil phase may further include a content of cyclic or linear silicone oils, or entirely consist of such oils. However, besides the silicone oil or oils, it is preferred to use an additional content of other oil phase components.

As silicone oil that is to be used in accordance with the invention, one advantageously uses cyclomethicone (octamethyl cyclotetrasiloxane). However, other silicone oils can also be used advantageously for the purposes of the present invention, for example, hexamethyl cyclotrisiloxane, polydimethylsiloxane, and poly(methylphenylsiloxane).

Other particularly advantageous mixtures are those of cyclomethicone and isotridecyl isononanoate, of cyclomethicone and 2-ethylhexyl isostearate.

The aqueous phase of the preparations according to the invention advantageously comprises, if need be, alcohols, diols, or polyols having a low number of C atoms, as well as their ethers, preferably ethanol, isopropanol, polypropylene glycol, glycerin, ethyleneglycol, ethyleneglycol monoethyl- or -monobutyl ether, polypropylene glycolmonomethyl, -monoethyl-, or -monobutyl ether, diethyleneglycol monomethyl- or -monoethyl ether, and analogous products, furthermore alcohols having a low number of C atoms, for example, ethanol, isopropanol, 1,2-propanediol, glycerin, as well as in particular one or more thickeners, which may advantageously be selected from the group of silicon dioxide, aluminum silicates, polysaccharides, or their derivatives, for example, hyaluronic acid, xanthan gum, hydroxypropylmethyl cellulose, very advantageously from the group of the polyacrylates, preferably a polyacrylate from the group of so-called Carbopols, for example, Carbopols of the grades 980, 981, 1382, 2984, 5984, each alone or in combination.

Gels according to the invention normally contain alcohols with a low number of C atoms, for example, ethanol, isopropanol, 1,2-propanediol, glycerin, and water, or an aforesaid oil in the presence of a thickener, which is in the case of oily-alcoholic gels preferably silicon dioxide or an aluminum silicate, in the case of aqueous-alcoholic or alcoholic gels preferably a polyacrylate.

Solid sticks contain, for example, natural or synthetic waxes, fatty alcohols, or fatty acid esters.

Customary parent substances that are suitable for the use as cosmetic sticks for the purposes of the present invention, are liquid oils (for example, paraffin oils, castor oils, isopropyl myristate), semisolid ingredients (for example, vaseline, lanolin), solid constituents (for example, beeswax, ceresine, and microcrystalline waxes or ozokerite), as well as high-melting waxes (for example, carnauba wax, candelilla wax).

Suitable as propellant for cosmetic and/or dermatological preparations for the purposes of the invention, that can be sprayed from aerosol containers, are the common, known, highly volatile, liquefied propellants, for example, hydrocarbons (propane, butane, isobutane), which can be used alone or mixed with one another. It is likewise advantageous to use compressed air.

Naturally, the skilled person is aware that there are per se nontoxic propellant gases that would basically be suitable for realizing the present invention in the form of aerosol preparations, but which ought to be nonetheless abandoned because of critical effects on the environment or other attendant circumstances, in particular fluorocarbons and fluorochlorinated hydrocarbons.

Cosmetic preparations for the purposes of the present invention can also be present as gels that contain besides an effective content of the active constituent according to the invention and the solvents as are normally used to this end, preferably water, in addition, organic thickeners, for example, gum arabic, xanthan gum, sodium alginate, cellulose derivatives, preferably methyl cellulose, hydroxymethyl cellulose, hydroxyethyl cellulose, hydroxypropyl cellulose, hydroxypropylmethyl cellulose, or inorganic thickeners, for example, aluminum silicates, such as betonite, or a mixture of polyethylene glycol and polyethyleneglycol stearate or -distearate. The thickener is contained in the gel, for example, in a quantity from 0.1 to 30 wt. %, preferably 0.5 to 15 wt. %.

Last but not least, it is possible and advantageous in accordance with the invention to use the preparations of the invention containing the active constituent or extract of the invention, for impregnating textiles (for example, cloths, pads) or adhesive strips (for example, medicated patches).

The following examples are to illustrate embodiments of the present invention. Unless otherwise specified, the numerical values will always refer to percentages by weight.

EXAMPLES OF O/W CREAMS

Example 1

| | |
|---|---|
| Glyceryl stearate, self-emulsifying | 4.00 |
| PEG-40 stearate | 1.00 |
| Cetyl alcohol | 3.00 |
| Caprylic-/capric triglyceride | 5.00 |
| Parrafinum liquidum | 5.00 |
| Licochalcone A | 0.05 |
| Tocopherol | 0.1 |
| Na₃HEDTA | 0.1 |
| Preservative, perfume | q.s. |
| Polyacrylic acid | 3.00 |
| Sodium hydroxide solution 45% | q.s. |
| Glycerin | 5.00 |
| Water | ad 100 |

Example 2

| | |
|---|---|
| Glycryl stearate, self-emulsifying | 3.00 |
| Stearic acid | 1.00 |
| Cetyl alcohol | 2.00 |
| Caprylic-/capric triglyceride | 3.00 |
| Dicaprylyl ether | 4.00 |
| Parraffinum liquidum | 2.00 |
| Licochalcone A | 0.01 |
| Preservative, perfume | q.s. |
| Polyacrylic acid | 0.10 |
| Sodium hydroxide solution 45% | q.s. |
| Glycerin | 3.00 |
| Butylene glycol | 3.00 |
| Water | ad 100 |

Example 3

| | |
|---|---|
| Glyceryl stearate citrate | 2.00 |
| Stearyl alcohol | 2.00 |
| Lanolin alcohol | 1.00 |
| Caprylic-/capric triglyceride | 4.00 |
| Paraffinum liquidum | 8.00 |
| Dimethicone | 1.00 |
| Licochalcone A | 0.04 |
| Preservative, perfume | q.s. |
| Sodium hydroxide solution 45% | q.s. |
| Glycerin | 7.50 |
| Water | ad 100 |

Example 4

| | |
|---|---|
| Glyceryl stearate citrate | 2.00 |
| Stearyl alcohol | 2.00 |
| Lanolin alcohol | 1.00 |
| Caprylic-/capric triglyceride | 4.00 |
| Paraffinum liquidum | 8.00 |
| Dimethicone | 1.00 |
| Licochalcone A | 0.03 |
| Preservative, perfume | q.s. |
| Sodium hydroxide solution 45% | q.s. |
| Glycerin | 7.50 |
| Dihydroxyacetone | 1.00 |
| Water | ad 100 |

Example 5

| | |
|---|---|
| Polyglyceryl-3-methylglucose distearate | 3.00 |
| Cetyl alcohol | 3.00 |
| Caprylic-/capric triglyceride | 3.00 |
| Dicapryl ether | 2.00 |
| Paraffinum liquidum | 3.00 |
| Licochalcone A | 0.25 |
| Na₃HEDTA | 0.10 |
| Preservative, perfume | q.s. |
| Polyacrylic acid | 0.10 |
| Sodium hydroxide solution 45% | q.s. |
| Glycerin | 3.00 |
| Water | ad 100 |

Example 6

| | |
|---|---|
| Glyceryl stearate citrate | 2.00 |
| Sorbitane stearate | 2.00 |
| Cetylstearyl alcohol | 2.00 |
| Caprylic-/capric triglyceride | 3.00 |
| Octyldodecanol | 2.00 |
| Dicapryl ether | 1.00 |
| Licochalcone A | 0.0125 |
| Tocopherol | 0.20 |
| Preservative, perfume | q.s. |
| Polyacrylic acid | 0.1 |
| Sodium hydroxide solution 45% | q.s. |
| Glycerin | 3.00 |
| Water | ad 100 |

EXAMPLES OF O/W CREAMS

Example 7

| | |
|---|---|
| Glyceryl stearate, self-emulsifying | 5.00 |
| Stearyl alcohol | 2.00 |
| Caprylic-/capric triglyceride | 2.00 |
| Octyldodecanol | 2.00 |
| Dimethicone polydimethylsiloxane | 2.00 |
| Titanium dioxide | 2.00 |
| 4-methylbenzylidene camphor | 1.00 |
| Butylmethoxy dibenzolymethane | 0.50 |
| Licochalcone A | 0.02 |
| Preservative, perfume | q.s. |
| Polyacrylic acid | 0.15 |
| Sodium hydroxide solution 45% | q.s. |
| Glycerin | 3.00 |
| Water | ad 100 |

Example 8

| | |
|---|---|
| Glyceryl stearate citrate | 2.00 |
| Cetylstearyl alcohol | 3.00 |
| C$_{12-15}$ alkylbenzoate | 2.00 |
| Octyldodecanol | 2.00 |
| Paraffinum liquidum | 4.00 |
| Licochalcone A | 0.125 |
| 2,4-bis-(4-(2-ethyl-hexyloxy-)2-hydroxyl-phenyl)-6-(4-methoxyphyenyl)-(1,3,5)-triazine | 1.00 |
| Dihydroxyacetone | 0.50 |
| Preservative, perfume | q.s. |
| Polyacrylic acid | 0.1 |
| Sodium hydroxide solution 45% | q.s. |
| Butylene glycol | 3.00 |
| Ethanol | 3.00 |
| Water | ad 100 |

Example 9

| | |
|---|---|
| Glyceryl stearate citrate | 2.00 |
| Cetyistearyl alcohol | 1.00 |
| C$_{12-15}$ alkylbenzoate | 3.00 |
| Paraffinum liquidum | 2.00 |
| Licochalcone A | 0.05 |

-continued

| | |
|---|---|
| 2,4-bis-(4-(2-ethyl-hexyloxy-)2-hydroxyl-phenyl)-6-(4-methoxyphenyl)-(1,3,5)-triazine | 3.00 |
| Ethylenediaminetetraacetic acid trisodium | 0.2. |
| Preservative, perfume | q.s. |
| Xanthan gum | 0.20 |
| Sodium hydroxide solution 45% | q.s. |
| Glycerin | 3.00 |
| Water | ad 100 |

Example 10

| | |
|---|---|
| Stearic acid | 2.50 |
| Cetyl alcohol | 3.00 |
| Octyldodecanol | 4.00 |
| Cyclic dimethylpolysiloxane | 0.50 |
| Licochalcone A | 0.20 |
| Preservative, perfume | q.s. |
| Polyacrylic acid | 0.05 |
| Sodium hydroxide solution 45% | q.s. |
| Glycerin | 5.00 |
| Ethanol | 3.00 |
| Water | ad 100 |

Example 11

| | |
|---|---|
| Stearic acid | 3.50 |
| Cetyl alcohol | 4.50 |
| Cetylstearyl alcohol | 0.50 |
| Octyldodecanol | 6.00 |
| Cyclic dimethylpolysiloxane | 2.00 |
| 4-methylbenzylidene camphor | 1.00 |
| Butylmethoxy dibenzoylmethane | 0.50 |
| Licochalcone A | 0.10 |
| 2,4-bis-(4-(2-ethyl-hexyloxy-)2-hydroxyl-phenyl)-6-(4-methoxyphenyl)-(1,3,5)-triazine | 0.50 |
| Dihydroxyacetone | 0.50 |
| Tocopherol | 0.05 |
| Ethylenediaminetetraacetic acid trisodium | 0.20 |
| Preservative, perfume | q.s. |
| Polyacrylic acid | 0.05 |
| Sodium hydroxidee solution 45% | q.s. |
| Glycerin | 3.00 |
| Water | ad 100 |

EXAMPLES OF W/O EMULSIONS

Example 12

| | |
|---|---|
| Polyglyceryl-2-dipolyhydroxy stearate | 5.00 |
| 2,4-bis-(4-(2-ethyl-hexyloxy-)2-hydroxyl-phenyl)-6-(4-methoxyphenyl)-(1,3,5)-triazine | 2.00 |
| Diethylhexyl butamido triazone | 3.00 |
| Octocrylene | 7.00 |
| Diethylhexyl butamido triazone | 1.00 |
| Phenylene-1,4-bis(monosodium)-2-benzimideazyl-5,7-disulfonic acid | 1.00 |
| Phenylbenzimidazole sulfonic acid | 0.50 |
| Zinc oxide | 3.00 |
| Dicapryl ether | 10.00 |
| Dicapryl carbonate | 5.00 |

-continued

| | |
|---|---|
| Phenylmethylpolysiloxane | 2.00 |
| PVP hexadecene copolymer | 0.50 |
| Glycerin | 3.00 |
| Magnesium sulfate | 1.00 |
| Tocopherol acetate | 0.50 |
| Licochalcone A | 0.05 |
| Preservative, perfume | q.s. |
| Ethanol | 3.00 |
| Water | ad 100 |

Example 13

| | |
|---|---|
| Cetyldimethicone copolyol | 2.50 |
| 2-ethylhexyl methoxycinnamate | 8.00 |
| 2,4-bis-(4-(2-ethyl-hexyloxy-)2-hydroxy)-phenyl)-6-(4-methoxyphenyl)-(1,3,5)-triazine | 2.50 |
| Diethylhexyl butamido triazone | 1.00 |
| 4-methylbenzylidene camphor | 2.00 |
| Octocrylene | 2.50 |
| Phenylene-1,4-bis(monosodium)-2-benzimideazyl-5,7-disulfonic acid | 2.00 |
| Titanium dioxide | 2.00 |
| Zinc oxide | 1.00 |
| Dimethicone polydimethylsiloxane | 4.00 |
| Phenylmethylpolysiloxane | 25.00 |
| Octoxyglycerin | 0.30 |
| Glycerin | 7.50 |
| Glycine soya | 1.00 |
| Magnesium sulfate | 0.50 |
| Licochalcone A | 0.02 |
| Preservative, perfume | q.s. |
| Water | ad 100 |

Example 14

| | |
|---|---|
| PEG-30-dipolyhydroxy stearate | 5.00 |
| Butylmethoxy dibenzoylmethane | 2.00 |
| Ethylhexyl triazone | 3.00 |
| Octocrylene | 4.00 |
| Phenylene-1,4-bis(monosodium)-2-benzimideazyl-5,7-disulfonic acid | 0.50 |
| Titanium dioxide | 1.50 |
| Zinc oxide | 2.00 |
| Paraffinum liquidum | 10.00 |
| Butyleneglycol dicaprylate-/dicaprate | 2.00 |
| Dicaprylylcarbonate | 6.00 |
| Dimethicone polydimethylsiloxane | 1.00 |
| Shea butter | 3.00 |
| Octoxyglycerin | 1.00 |
| Glycine soya | 1.50 |
| Magnesium chloride | 1.00 |
| Tocopherolacetate | 0.25 |
| Licochalcone A | 0.125 |
| Preservative, perfume | q.s. |
| Ethanol | 1.50 |
| Water | ad 100 |

Example 15

| | |
|---|---|
| Cetyldimethicone copolyol | 4.00 |
| 2-ethylhexyl methoxycinnamate | 5.00 |

-continued

| | |
|---|---|
| 2,4-bis-(4-(2-ethyl-hexyloxy-)2-hydroxy)-phenyl)-6-(4-methoxyphenyl)-(1,3,5)-triazine | 2.00 |
| Butylmethoxy dibenzoylmethane | 1.00 |
| Ethylhexyl triazone | 4.00 |
| 4-methylbenzylidene camphor | 4.00 |
| Diethylhexyl butamido triazone | 2.00 |
| Phenylbenzimidazole sulfonic acid | 3.00 |
| Zinc oxide | 0.50 |
| $C_{12-15}$ alkylbenzoate | 9.00 |
| Butyleneglycol dicaprylate-/dicaprate | 8.00 |
| Dimethicone polydimethylsiloxane | 5.00 |
| PVP hexadecene copolymer | 0.50 |
| Glycerin | 7.50 |
| Magnesium sulfate | 0.50 |
| Licochalcone A | 0.20 |
| Preservative, perfume | q.s. |
| Water | ad 100 |

Example 16

| | |
|---|---|
| Polyglyceryl-2-dipolyhydroxy stearate | 4.50 |
| 2-ehylhexyl methoxycinnamate | 4.00 |
| 2,4-bis-(4-(2-ethyl-hexyloxy-)2-hydroxy)-phenyl)-6-(4-methoxyphenyl)-(1,3,5)-triazine | 2.50 |
| Diethyihexyl butamido triazone | 3.00 |
| Ethylhexyl triazone | 2.00 |
| 4-methylbenzylidene camphor | |
| Octocrylene | 2.50 |
| Phenylbenzimidazole sulfonic acid | 2.00 |
| Titanium dioxide | 3.00 |
| Paraffinum liquidum | 8.00 |
| Dicaprylyl ether | 7.00 |
| Butyleneglycol dicaprylate-/dicaprate | 4.00 |
| Phenylmethylpolysiloxane | 2.00 |
| PVP hexadecane copolymer | 1.00 |
| Octoxyglycerin | 0.50 |
| Glycerin | 2.50 |
| Magnesium chloride | 0.70 |
| Tocopherolacetate | 1.00 |
| Licochalcone A | 0.25 |
| Preservative, perfume | q.s. |
| Ethanol | 1.00 |
| Water | ad 100 |

EXAMPLES OR W/O EMULSIONS

Examples

| | 17 | 18 |
|---|---|---|
| Polyglyceryl-2-dipolyhydroxy stearate | 4.00 | 5.00 |
| Lanolin alcohol | 0.50 | 1.50 |
| Isohexadecane | 1.00 | 2.00 |
| Myristyl mirystate | 0.50 | 1.40 |
| Vaseline | 1.00 | 2.00 |
| Butylmethoxy dibenzoylmethane | 0.50 | 1.50 |
| 4-methylbenzylidene camphor | 1.00 | 3.00 |
| Butyleneglycol dicaprylate/-dicaprate | 4.00 | 5.00 |
| Shea butter | — | 0.50 |
| Butyleneglycol | — | 6.00 |
| Octoxyglycerin | — | 3.00 |
| Glycerin | 5.00 | — |
| Tocopherolacetate | 0.50 | 1.00 |
| Licochalcone A | 0.20 | 0.10 |
| EDTA | 0.20 | 0.20 |
| Preservative | q.s. | q.s. |

-continued

|  | 17 | 18 |
|---|---|---|
| Ethanol | — | 3.00 |
| Perfume | q.s. | q.s. |
| Water | ad 100 | ad 100 |

EXAMPLE OF W/O CREAM

Example 19

| | |
|---|---|
| Polyglyceril-3-diisostearate | 3.50 |
| Glycerin | 3.00 |
| Polyglyceryl-2-dipolyhydroxy stearate | 3.50 |
| Licochalcone A | 0.10 |
| Preservative | q.s. |
| Perfume | q.s. |
| Magnesium sulfate | 0.6 |
| Isopropylstearate | 2.0 |
| Caprylylether | 8.0 |
| Cetearylisononanoate | 6.0 |
| Water | ad 100 |

EXAMPLE OF W/O EMULSION

Example 20

| | |
|---|---|
| Triceteareth-4-phosphate | 0.80 |
| Butylhydroxytoluene | 0.05 |
| Glyceryllanolate | 1.70 |
| Cyclomethicone | 2.20 |
| Isopropylpalmitate | 1.00 |
| Licochalcone A | 0.10 |
| Polyacrylic acid | 0.50 |
| Ethylenediaminetetraacetic acid | 1.00 |
| Sodium hydroxide | q.s. |
| Citric acid | 0.01 |
| Preservative | q.s. |
| Perfume | q.s. |
| Water | ad 100 |

What is claimed is:

1. A method of treating rosacea in a subject having rosacea, comprising topically applying a therapeutically effective amount of Licochalcone A to an area of the subject in need of treatment of the rosacea.

2. The method of claim 1, wherein the Licochalcone A is applied in the form of a cosmetic or dermatological preparation which comprises Licochalcone A.

3. The method of claim 2, wherein the preparation comprises Licochalcone A in a concentration of from 0.0001 wt. % to 5 wt. %, based on a total weight of the preparation.

4. The method of claim 3, wherein Licochalcone A is present in a concentration of from 0.001 wt. % to 1 wt. %.

5. The method of claim 1, wherein the Licochalcone A is applied in the form of a cosmetic or dermatological preparation which comprises an aqueous extract of Radix Glycyrrhiza inflata.

6. The method of claim 5, wherein the aqueous extract is present in a concentration of from 0.001 wt. % to 10 wt. %, based on a total weight of the preparation.

7. The method of claim 6, wherein the aqueous extract is present in a concentration of from 0.01 wt. % to 2 wt. %.

8. The method of claim 2, wherein the preparation further comprises one or more polyols.

9. The method of claim 8, wherein the one or more polyols comprise at least one of butylene glycol and glycerol.

10. The method of claim 8, wherein the one or more polyols are present in a concentration of from 0.001 wt. % to 10 wt. %, based on a total weight of the preparation.

11. The method of claim 10, wherein the one or more polyols are present in a concentration of from 0.05 wt. % to 5 wt. %.

12. The method of claim 2, wherein the preparation further comprises water.

13. A method of treating rosacea in a subject having rosacea, comprising topically applying a therapeutically effective amount of an aqueous extract of Radix Glycyrrhiza inflata to an area of the subject in need of treatment of the rosacea.

14. The method of claim 13, wherein the aqueous extract is applied in the form of a cosmetic or dermatological preparation.

15. The method of claim 14, wherein the aqueous extract is present in a concentration of from 0.001 wt. % to 10 wt. %, based on a total weight of the preparation.

16. The method of claim 15, wherein the aqueous extract is present in a concentration of from 0.01 wt. % to 2 wt. %.

17. The method of claim 14, wherein the preparation further comprises one or more polyols.

18. The method of claim 17, wherein the one or more polyols comprise at least one of butylene glycol and glycerol.

19. The method of claim 17, wherein the one or more polyols are present in a concentration of from 0.001 wt. % to 10 wt. %, based on a total weight of the preparation.

20. The method of claim 19, wherein the one or more polyols are present in a concentration of from 0.05 wt. % to 5 wt. %.

* * * * *